(12) United States Patent
Gilad et al.

(10) Patent No.: US 8,639,314 B2
(45) Date of Patent: Jan. 28, 2014

(54) DEVICE, SYSTEM AND METHOD FOR IN-VIVO IMAGING OF A BODY LUMEN

(75) Inventors: Zvika Gilad, Haifa (IL); Amit Pascal, Haifa (IL)

(73) Assignee: Given Imaging Ltd., Yoqneam (IL)

( * ) Notice: Subject to any disclaimer, the term of this patent is extended or adjusted under 35 U.S.C. 154(b) by 1644 days.

(21) Appl. No.: 11/284,915

(22) Filed: Nov. 23, 2005

(65) Prior Publication Data

US 2007/0129624 A1 Jun. 7, 2007
US 2011/0034795 A9 Feb. 10, 2011

Related U.S. Application Data

(63) Continuation-in-part of application No. PCT/IL2004/001153, filed on Dec. 22, 2004.

(60) Provisional application No. 60/531,997, filed on Dec. 24, 2003.

(51) Int. Cl.
*A61B 5/00* (2006.01)

(52) U.S. Cl.
USPC .......................................... 600/407; 600/473

(58) Field of Classification Search
USPC .......... 600/101, 109, 129, 130, 160, 302, 407
See application file for complete search history.

(56) References Cited

U.S. PATENT DOCUMENTS

| | | | |
|---|---|---|---|
| 3,683,389 A | 8/1972 | Hollis | |
| 3,971,362 A | 7/1976 | Pope et al. | |
| 4,149,769 A | 4/1979 | Zobel | |
| 4,217,045 A | 8/1980 | Ziskind | |
| 4,278,077 A | 7/1981 | Mizumoto | |
| 4,572,616 A | 2/1986 | Kowel et al. | |
| 4,588,294 A | 5/1986 | Siegmund | |
| 4,596,050 A | 6/1986 | Rogers | |
| 4,689,621 A | 8/1987 | Kleinberg | |
| 4,741,327 A | 5/1988 | Yabe | |
| 4,844,076 A | 7/1989 | Lesho et al. | |
| 4,867,136 A | 9/1989 | Suzuki et al. | |
| 4,951,135 A | 8/1990 | Sasagawa et al. | |

(Continued)

FOREIGN PATENT DOCUMENTS

| | | |
|---|---|---|
| DE | 34 40 177 | 5/1986 |
| DE | 10028155 | 12/2000 |

(Continued)

OTHER PUBLICATIONS

International Search Report for International application No. PCT/IL06/01331 mailed Jan. 17, 2008.

(Continued)

*Primary Examiner* — Peter Luong
(74) *Attorney, Agent, or Firm* — Pearl Cohen Zedek Latzer Baratz LLP

(57) ABSTRACT

An in-vivo device, system and a method for imaging a body lumen, typically liquid filled body lumen. The in-vivo device may have a specific gravity of about 1 or a volume to weight ratio that enables it to float. The in-vivo device may include an optical system for viewing through a body lumen liquid and another optical system for viewing through a non liquid medium. The in-vivo device may be moved through the body lumen by the liquid movement in that lumen.

20 Claims, 7 Drawing Sheets

(56) References Cited

U.S. PATENT DOCUMENTS

| | | | |
|---|---|---|---|
| 5,279,607 | A | 1/1994 | Schentag et al. |
| 5,381,784 | A | 1/1995 | Adair |
| 5,395,366 | A | 3/1995 | D'Andrea et al. |
| 5,459,605 | A | 10/1995 | Kempf |
| 5,575,754 | A | 11/1996 | Konomura |
| 5,603,687 | A | 2/1997 | Hori et al. |
| 5,604,531 | A | 2/1997 | Iddan et al. |
| 5,643,175 | A | 7/1997 | Adair |
| 5,754,313 | A | 5/1998 | Pelchy et al. |
| 5,819,736 | A | 10/1998 | Avny et al. |
| 5,833,603 | A | 11/1998 | Kovacs et al. |
| 5,940,126 | A | 8/1999 | Kimura |
| 5,986,693 | A | 11/1999 | Adair et al. |
| 5,993,378 | A | 11/1999 | Lemelson |
| 6,165,128 | A | 12/2000 | C'espedes et al. |
| 6,184,923 | B1 | 2/2001 | Miyazaki |
| 6,211,904 | B1 | 4/2001 | Adair et al. |
| 6,240,312 | B1 | 5/2001 | Alfano et al. |
| 6,310,642 | B1 | 10/2001 | Adair et al. |
| 6,692,430 | B2 | 2/2004 | Adler |
| 6,800,060 | B2 | 10/2004 | Marshall |
| 6,939,295 | B2 * | 9/2005 | Yokoi et al. .................... 600/176 |
| 7,192,397 | B2 * | 3/2007 | Lewkowicz et al. .......... 600/160 |
| 2001/0017649 | A1 | 8/2001 | Yaron |
| 2001/0035902 | A1 | 11/2001 | Iddan et al. |
| 2001/0051766 | A1 | 12/2001 | Gazdzinski |
| 2002/0103417 | A1 | 8/2002 | Gazdzinski |
| 2002/0109774 | A1 * | 8/2002 | Meron et al. .................... 348/74 |
| 2002/0158976 | A1 | 10/2002 | Avni et al. |
| 2002/0173718 | A1 | 11/2002 | Frisch et al. |
| 2002/0198439 | A1 | 12/2002 | Mizuno |
| 2003/0018280 | A1 | 1/2003 | Lewkowicz et al. |
| 2003/0023150 | A1 | 1/2003 | Yokoi et al. |
| 2003/0028078 | A1 | 2/2003 | Glukhovsky |
| 2003/0114742 | A1 | 6/2003 | Lewkowicz et al. |
| 2003/0120130 | A1 | 6/2003 | Glukhovsky et al. |
| 2003/0171649 | A1 | 9/2003 | Yokoi et al. |
| 2003/0214726 | A1 | 11/2003 | Mihara |
| 2003/0227547 | A1 | 12/2003 | Iddan |
| 2004/0181155 | A1 * | 9/2004 | Glukhovsky .................. 600/476 |
| 2004/0249247 | A1 | 12/2004 | Iddan |
| 2004/0254455 | A1 | 12/2004 | Iddan |
| 2005/0043583 | A1 | 2/2005 | Killmann et al. |
| 2007/0106112 | A1 | 5/2007 | Gat et al. |

FOREIGN PATENT DOCUMENTS

| | | |
|---|---|---|
| EP | 0228493 | 3/1991 |
| IL | 110475 | 11/2000 |
| JP | 57-45833 | 3/1982 |
| JP | HEI3-289779 | 12/1991 |
| JP | 4-109927 | 4/1992 |
| JP | 1992-144533 | 5/1992 |
| JP | HEI4-180736 | 6/1992 |
| JP | 5015515 | 1/1993 |
| JP | 7289504 | 11/1995 |
| JP | 2001-137182 | 5/2001 |
| JP | 2001/224551 | 8/2001 |
| JP | 2001/224553 | 8/2001 |
| JP | 2003-260025 | 9/2003 |
| WO | WO 92/21307 | 12/1992 |
| WO | WO 98/37796 | 11/1996 |
| WO | WO 98/11816 | 3/1998 |
| WO | WO 98/51993 | 11/1998 |
| WO | WO 00/22975 | 4/2000 |
| WO | WO 00/76391 | 12/2000 |
| WO | WO 01/08548 | 2/2001 |
| WO | WO 01/50180 | 7/2001 |
| WO | WO 01/50941 | 7/2001 |
| WO | WO 01/65995 | 9/2001 |
| WO | WO 02/054932 | 7/2002 |
| WO | WO 02/055126 | 7/2002 |
| WO | WO 02/067593 | 8/2002 |
| WO | WO 02/094337 | 11/2002 |
| WO | WO 02/102224 | 12/2002 |
| WO | WO 03/003706 | 1/2003 |
| WO | WO 03/011103 | 2/2003 |
| WO | WO 2004/028335 | 4/2004 |
| WO | WO 2004/028336 | 4/2004 |
| WO | WO 2004/054430 | 7/2004 |

OTHER PUBLICATIONS

U.S. Appl. No. 10/046,541, filed Jan. 16, 2002, Meron et al.
U.S. Appl. No. 10/836,614, filed May 3, 2004, Iddan.
U.S. Appl. No. 10/811,013, filed Mar. 29, 2004, Iddan.
U.S. Appl. No. 10/213,345, filed Aug. 7, 2002, Glukhovsky.
U.S. Appl. No. 60/312,081, filed Aug. 15, 2001, Ashery et al.
The Radio Pill, Rowlands, et al., British Communications and Electronics, Aug. 1960, pp. 598-601.
Wellesley company sends body montiors into space—Crum, Apr. 1998.
Wireless transmission of a color television moving image from the stomach using a miniature CCD camera, light source and microwave transmitter. Swain CP, Gong F, Mills TN. Gastrointest Endosc 1997;45:AB40.
BBC News Online—Pill camera to 'broadcast from the gut', Feb. 21, 2000, www.news.bbc.co.uk.
Office Communication. Date Mailed Oct. 20, 2004. U.S. Appl. No. 10/046,541.
Office Communication. Date Mailed May 19, 2005. U.S. Appl. No. 10/046,541.
Office Communication. Date Mailed Jan. 12, 2006. U.S. Appl. No. 10/046,541.
Office Action of U.S. Appl. No. 11/284,915 mailed on Sep. 3, 2008.
Office Action of U.S. Appl. No. 11/284,915 mailed on Mar. 17, 2009.
Office Action of European Application No. 04806684.9 mailed on Mar. 18, 2009.
Supplementary Partial European Search Report of European Application No. 04806684.9 dated Nov. 6, 2007.
International Search Report of Application No. PCT/IL04/01153 mailed Oct. 26, 2005.
Shin-Ichi et al: "Robots for the future", Nov. 29, 2001.
"Video Camera to Take", RF System Lab, Dec. 25, 2001.
www.rfnorkia.co-NORIKA3, Dec. 24, 2001.
Wang et al: "Integrated Micro-Instrumentation for dynamic Monitoring of the Gastro-Intestinal Tract", Presented at IEEE Instrumentaiton and Measurement Technology Conference, May 2002, Anchorage, AK, USA, www. See ed.ac.uk/Naa.publications.html.
Slater, Dan:Panaromic Photography with Fisheye Lenses, © Published in IAPP Journal, 1996.

* cited by examiner

DEVICE, SYSTEM AND METHOD FOR IN-VIVO IMAGING OF A BODY LUMEN

CROSS-REFERENCE TO RELATED APPLICATIONS

This application is a Continuation-In-Part of International Patent Application No. PCT/IL2004/01153, filed Dec. 22, 2004, which in turn claims priority of U.S. Provisional Patent Application No. 60/531,997, filed Dec. 24, 2003.

FIELD OF THE INVENTION

The present invention relates to the field of in-vivo diagnostics. More specifically, the present invention relates to a device, system and method for imaging a body lumen.

BACKGROUND OF THE INVENTION

Known devices may be helpful in providing in-vivo imaging. Autonomous in-vivo imaging devices, such as swallowable or ingestible capsules or other devices may move through a body lumen, imaging as they move along. Some of these devices use a wireless connection to transmit image data. Some in-vivo imaging devices have a limited field-of-view. Some desirable portions of an in-vivo lumen may not be imaged with such fields of view.

SUMMARY OF THE INVENTION

There is thus provided, according to embodiments of the invention, a device, system and method for imaging a body lumen. According to an embodiment of the invention there is provided a device, system and method for imaging typically voluminous, usually liquid filled body lumens, for example, the stomach.

According to an embodiment of the invention a typically floatable imaging device, or a device having other suitable weight or mass distribution or specific gravity, is moved through a body lumen, such as the large intestine or stomach, by using the passage of a volume of liquid within and/or through the body lumen.

According to embodiments of the invention, the floatable in-vivo imaging device, may have a specific gravity of about 1 or less, or a volume to weight ratio that enables it essentially to float, for example, in a body lumen liquid, for example the liquid typically found in the human stomach, or for example liquid that may be administered to a patient to fill a lumen such as the stomach.

According to an embodiment of the invention the floatable imaging device may be inserted in-vivo. For example, a typically autonomous floatable device may be ingested and moved through the GI tract, typically by peristalsis. When reaching a relatively voluminous liquid filled lumen, such as the stomach, the device, which may float in the volume of liquid, may be moved through the lumen in accordance with the movement of the volume of liquid. Other embodiments may include other suitable devices and methods.

According to a further embodiment of the invention there is provided a method for imaging body lumens, such as the large intestine or the stomach. The method according to one embodiment of the invention comprises the step of inserting a floatable in-vivo device into a patient lumen, for example by swallowing the imaging device, preferably after which a patient ingests a volume of liquid, for example water or juice. In an embodiment of the invention the method is used for imaging the stomach and may comprise the step of ingesting a composition to retrain liquids in the body lumen.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features and advantages thereof, may best be understood by reference to the following detailed description when read with the accompanied drawings in which:

Figure 1A:
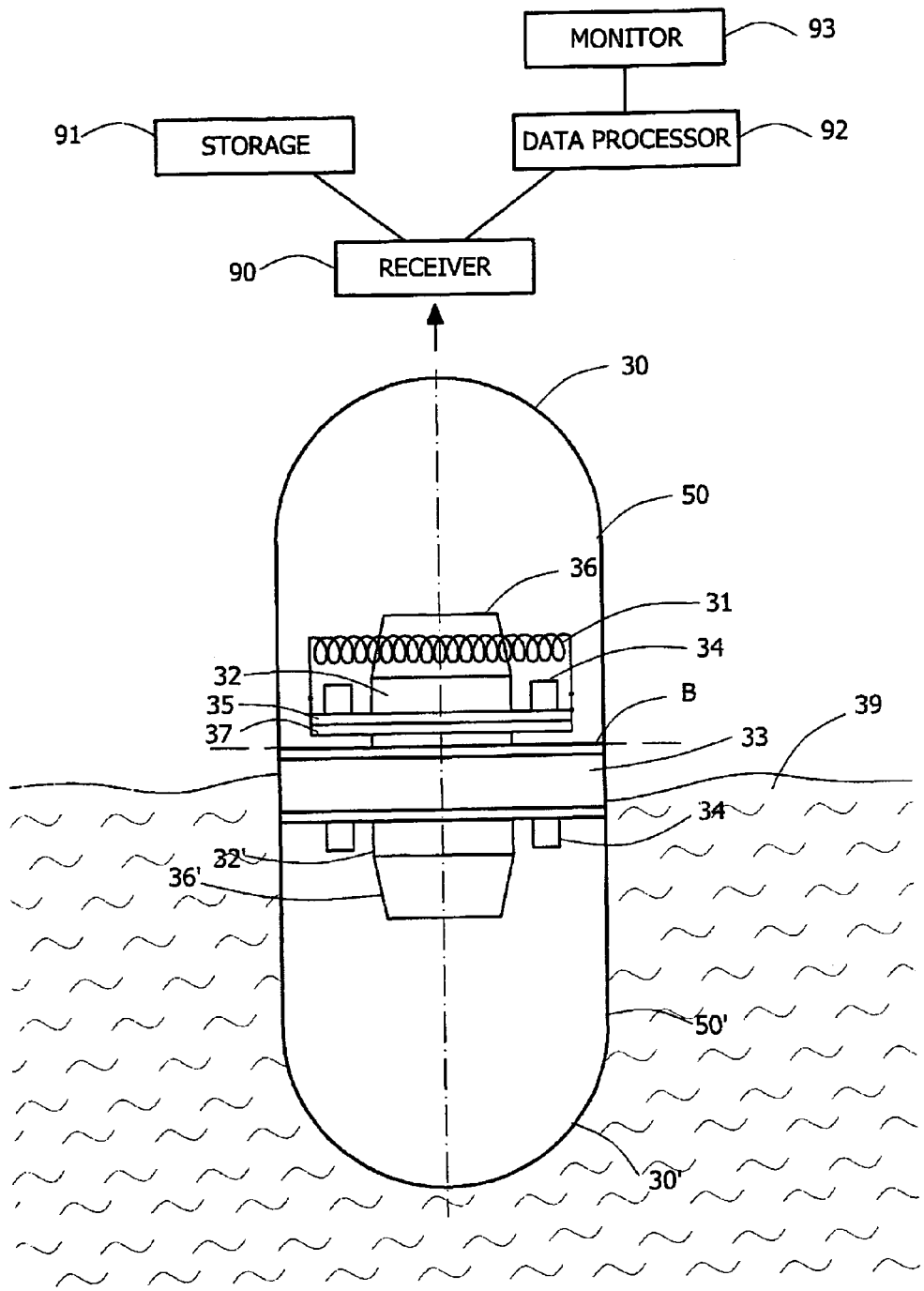
FIG. 1A is a schematic diagram of an embodiment of an in-vivo imaging device and an external receiver and transmitter system in accordance with an embodiment of the invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements

DETAILED DESCRIPTION OF THE INVENTION

In the following description, various aspects of the present invention will be described. For purposes of explanation, specific configurations and details are set forth in order to provide a thorough understanding of the present invention. However, it will also be appreciated by one skilled in the art that the present invention may be practiced without the specific details presented herein. Furthermore, well known features may be omitted or simplified in order not to obscure the present invention.

Reference is now made to FIG. 1A, which schematically illustrates an in-vivo imaging device and system according to an embodiment of the present invention. An embodiment of the present invention may provide a floatable in-vivo imaging device 40 that can be carried by liquid 39. According to some embodiments of the present invention, the imaging device 40 may be useful in imaging lumens containing or capable of containing a bulk of liquid 39.

According to one embodiment of the present invention, device 40 may include two optical heads, for example two transparent empty-spaced elongated optical domes 30 and 30' behind which are situated illumination sources 34, such as one or more LEDs (Light Emitting Diode), and/or OLEDs (Organic LED) or other illumination sources, two optical systems such as lens holders 32 and 32', two imagers 36 and 36' (such as for example a CMOS, a CCD, etc.) a transmitter 35 (such as an ASIC) and/or a receiver and a processor 37. The device 40 may further include power source(s) 33, which may provide power to the entirety of electrical elements of the device, an antenna 31 for transmitting and receiving, for example video signals from the imagers 36 and 36'. While two domes and optical systems are shown, other numbers, such as one or more than two (if device 40 is spherical shaped, for example), may be used According to some embodiments of the present invention, device 40 is capable of simultaneously obtaining images of the body lumen, for example, the stomach, from two ends of the device. For example, according to one embodiment of the present invention, device 40 may be a cylindrical capsule having a front end and a rear end, which is capable of passing the entire GI tract.

The elongated empty-spaced domes 30 and 30' may be for example hemispherical shaped optical domes having optical properties that are taken into account when designing the lens holders 32 and 32' such as for example setting the spacing between the lenses in the lens holders 32 and 32'.

According to some embodiments of the present invention device 40 may include suitable optical systems for viewing through a liquid as well as for viewing through a substantially non liquid medium. For example, a lens holder, such as lens holder 32 suitable for viewing through air (e.g. compatible with the refractive index of the air) may be placed behind transparent elongated optical dome 30 (which may be also suitable for viewing through air), while behind the transparent elongated optical dome 30' may be placed a lens holder, such as lens holder 32' suitable for viewing through liquid (e.g. compatible with the refractive index of the liquid)

According to one embodiment of the invention the in vivo imaging device has a specific gravity (SG) of about 1.0 or a volume to weight ratio that enables it essentially to float such that the imagers 36 and 36' may be oriented in a plane parallel to or substantially parallel to a short axis "B" of device 40, and/or may be perpendicular to or substantially perpendicular to long axis A. Deviations from "horizontal" and "vertical" positions, such as angling, from long axis A or short axis B may be used. When used herein, vertical and horizontal are relative terms, and may be interchangeable based on perspectives of the viewer, or based on specific embodiments.

According to some embodiments of the present invention, outside a patient's body may be, for example, an image receiver 90 (including, for example, an antenna or an antenna array), a storage unit 91, a data processor 92, and a monitor 93.

According to some embodiments of the present invention, device 40 may communicate with an external receiving and display system (e.g., through receiver 90) to provide display of data, control, or other functions For example, power may be provided to device 40 using an internal battery, an internal power source, or a wireless system to receive power. Other embodiments may have other configurations and capabilities. For example, components may be distributed over multiple sites or units, and control information may be received from an external source.

According to some embodiments of the present invention, device 40 typically may be or may include an autonomous swallowable capsule, but device 40 may have other shapes and need not be swallowable or autonomous. Embodiments of device 40 are typically autonomous, and are typically self-contained. For example, device 40 may be a capsule or other unit where all the components are substantially contained within a container or shell, and where device 40 does not require any wires or cables to, for example, receive power or transmit information. In one embodiment, all of the components may be sealed within the device body (the body or shell may include more than one piece); for example, the imagers 36 and 36', the illumination sources 34, the power source(s), and the transmitter, may all be sealed within the device body The system and method of the present invention may be used with or in an imaging system such as that described in U.S. patent application, Ser. No. 09/800,470, entitled A DEVICE AND SYSTEM FOR IN-VIVO IMAGING, filed on Mar. 8, 2001. A further example of an imaging system with which the system and method of the present invention may be used is described in U.S. Pat. No. 5,604,531 to Iddan et al., entitled IN-VIVO VIDEO CAMARA SYSTEM, filed on Jan. 17, 1995. Both these publications are assigned to the common assignee of the present application and are hereby incorporated by reference. Alternatively, the system of the present invention may be utilized in any suitable imaging device providing images of a body lumen or cavity For example, a circuit board according to an embodiment of the invention may be utilized in probes used for in-vivo imaging, such as endoscopes.

Figure 1B:
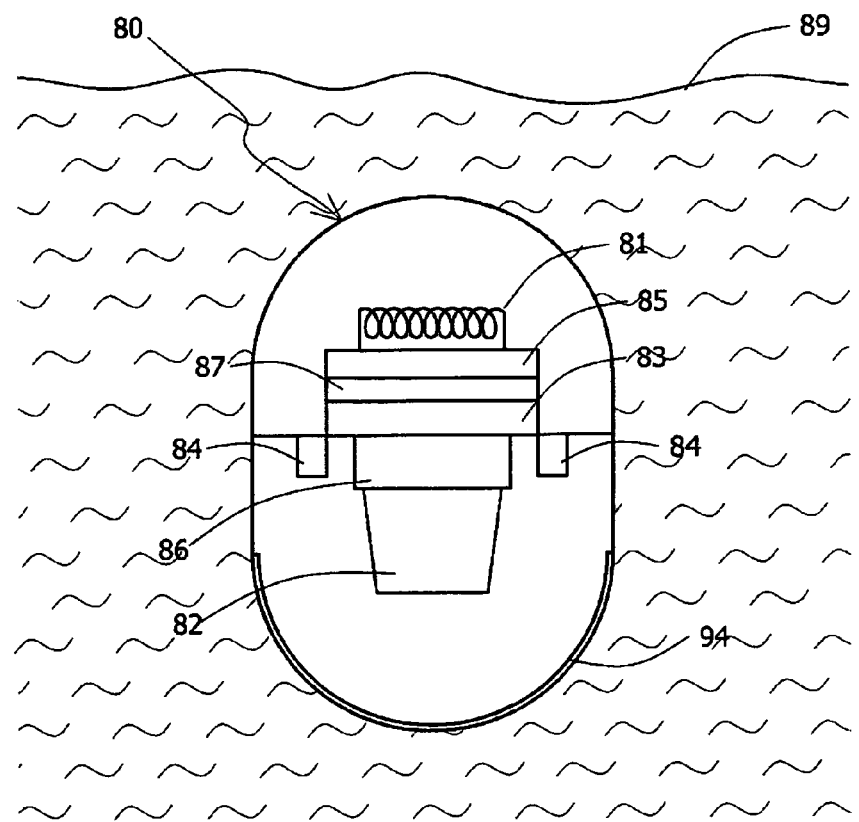
FIG. 1B is a schematic diagram of an embodiment of an in-vivo imaging device according to another embodiment of the present invention.

Reference is now made to FIG. 1B, which schematically illustrates an in-vivo imaging device according to another embodiment of the present invention. According to one embodiment of the present invention, device 80 may include an optical head, for example a transparent empty-spaced elongated optical dome 94 behind which are situated illumination sources 84, such as one or more LEDs (Light Emitting Diode), and/or OLEDs (Organic LED) or other illumination sources, an optical system such as a lens holder 82 and an imager 86 (such as for example a CMOS, a CCD, etc.) a transmitter 85 (such as an RF transmitter) and/or a receiver and a processor 87. The device 80 may further include power source(s) 83, which may provide power to the entirety of electrical elements of the device, an antenna 81 for transmitting and/or receiving. For example, the antenna may be used to transmit video signals from the imager 86.

According to some embodiments of the present invention device 80 may include suitable optical systems for viewing through liquid. For example, the lens holder 82 may be suitable for viewing through liquid (e.g. compatible with the refractive index of the liquid).

Figure 2:
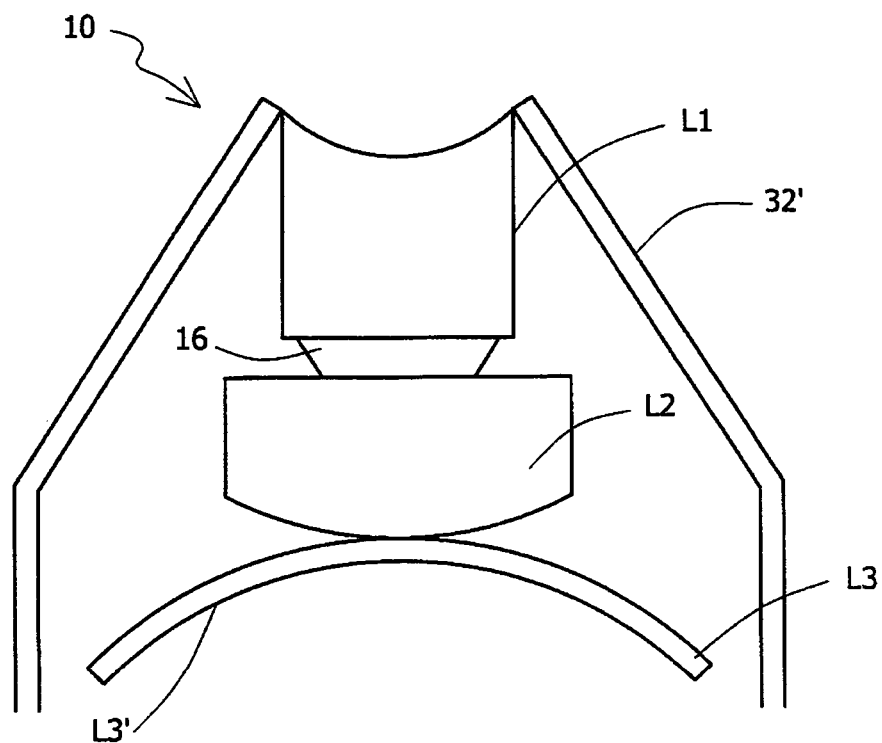
FIG. 2 is a schematic two dimensional presentation of an optical system according to an embodiment of the present invention.

According to some embodiments of the present invention, device 80 may be designed such the transparent empty-spaced elongated optical domes 94 will always be submerged in a liquid 89, such as, for example, a typical human stomach fluid, or fluid of other body parts. For example when device 80 reaches, for example, the stomach lumen the transparent empty-spaced elongated optical domes 94 bearing the optical system compatible for under water imaging will be submerged Reference is now made to FIG. 2, which is a schematic two dimensional presentation of an exemplary lens construction, according to an embodiment of the present invention. Referring to FIG. 2, the lens construction referenced as 10 may be provided in the lens holder 32' included in, for example, device 40 of FIG. 1, but may be included in other suitable devices, such as an endoscope, trocar, or other in-vivo imaging device. In the case of the particular example shown, the lens holder may include three lens elements L1, L2, and L3 suitable for viewing through liquid (e.g. compatible with the refractive index of liquid) The first lens L1 may be, for example a focusing lens such as a planoconcave lens having a flat lens surface on the side of the subject and a concave lens surface on the image-forming side. The second lens L2 which may be used for correcting aberrations may be, for example planoconvex lens L2 and may be located next to the first lens L1. Further, the third lens L3 may be a field lens such as a convex lens. Interposed between the first lens L1 and the second lens L2 may be for example an aperture, such as an aperture stop 16, which determines the amount of light which reaches an imager and/or an imager area such as imagers 36 and 36'.

According to some embodiments of the present invention, an optical design of a lens holder such as lens holder 32, suitable for viewing through air, may be provided, by replacing one of the lens elements L1, L2, and L3 of lens holder 32', or by changing the surface shape of one of the lens's. For example the lens construction of lens holder 32 may be formed by replacing lens L3 or by changing the surface L3' of lens L3. Thus, changing the refractive index and the optical design of the lens construction 10, e.g. from a lens construction suitable for viewing through liquid to a lens construction suitable for viewing through air According to some embodiments of the present invention, the refractive index and/or the optical design of a lens construction, such as lens construction 10, may be changed by using, for example an adaptive optical lens structure such as a low control voltage liquid crystals (LCs). According to one embodiment, the length of the adaptive optical lens may be tuned from one focal length to another focal length and may provide a sharp, clean image.

Figure 3:
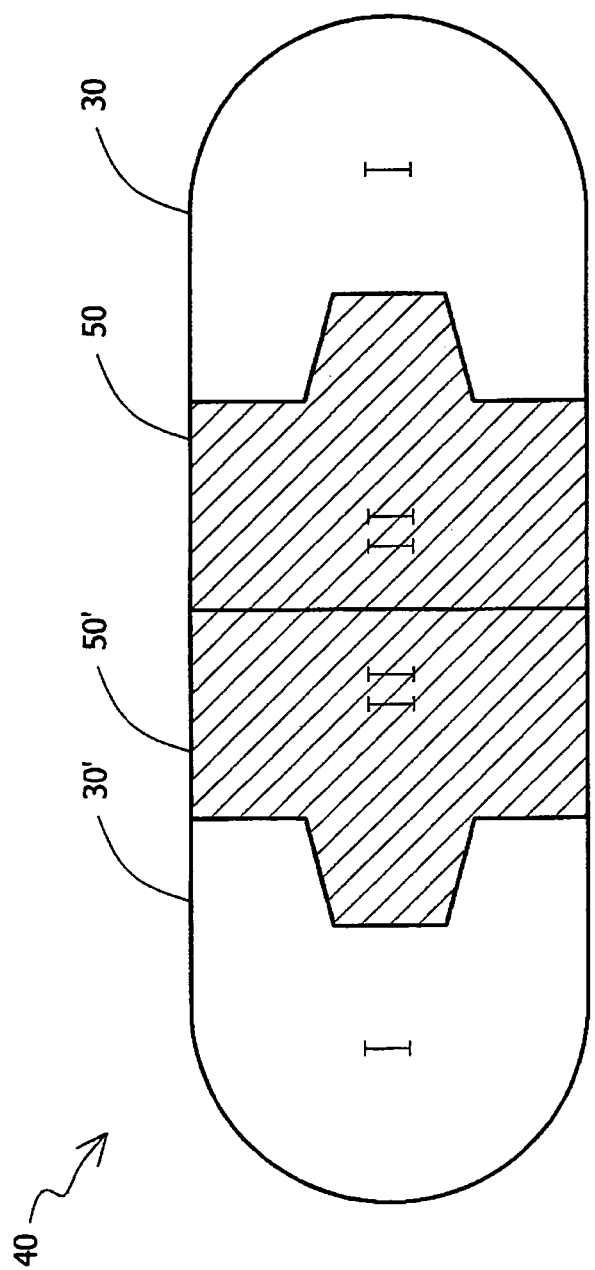
FIG. 3 is a schematic cross-sectional representation of volumes of space included in an in-vivo imaging device in accordance with an embodiment of the invention.

Reference is now made to FIG. 3, which depicts a schematic cross-sectional representation of volumes of space included in device 40. The elongated typically empty-spaced dome(s) 30 and 30' may include one or more volumes of space empty of components, for example spaces 1. According to some embodiments of the present invention, the volume(s) of spaces 1 may be each greater than twice the volume of a central volume of space 11 which may include components that may be located at or near the center of the imaging device 40. The components comprising the central volume of space 11 may typically be the lens holders 32 and 32', imagers 36 and 36' and components described hereinafter.

According to some embodiments of the present invention, device 40 may be designed such that one section of device 40, for example section 50 which may include the optical system which is suitable for viewing through a liquid 39, e.g optical dome 30' lens holder 32' and imager 36', will be submerged in a liquid 39, such as, for example, a typical human stomach fluid, or fluid of other body parts, while the other section of device 40, for example section 50' which may include optical dome 30' lens holder 32' and imager 36', will be exposed, bearing an optical system suitable for viewing through air which will be kept floating at all time.

According to some embodiments of the present invention, the center of gravity of device 40 is adjusted to ensure that one side of device 40, e g. section 50 will remain afloat while the other side, e.g. section 50' will be submerged when moving through the liquid 39. For example, the center of gravity may be set in the section, or in proximity to the section of the device 40 that we wish to keep submerged during the device 40 movement. The center of gravity may be set through the positioning of certain components of the device 40 in desired areas, or designing the device 40 in a way that ensures that the device 40 specific weight is compatible to the shape of the outer envelope, and thus both the head and tail of the device 40 such as the dome(s) 30 and 30 ' are at an angle perpendicular to the fluid. For example the components placed in the central volume of space 11 may be arranged in such a way which will result in a center of gravity located in proximity to the elongated optical dome 30', which was adapted and optimized for viewing and imaging through liquid.

According to one embodiment, the empty volume(s) I and/or the central volume of space II may render the device floatable in a liquid filled lumen.

According to one embodiment the floatable in-vivo imaging device 40 may include one or more buoyant bod(ies) or other weight, specific gravity, ballast or mass controlling system. The buoyant body, which may be attached to the floatable in-vivo imaging device 40 or which may optionally house the floatable in-vivo imaging device and/or one or more elements of the floatable in-vivo imaging device 40, may keep the in-vivo imaging device 40 essentially floating in a liquid filled body lumen for example, in a typical human stomach fluid. Embodiments including a floatable imaging device are described, for example, in U.S. application Ser. No. 10/150, 492 entitled "Floatable in-vivo Sensing Device and Method for Use" published on Jan. 23, 2003 which is assigned to the assignee of the present invention and which is hereby incorporated by reference. Other suitable specific gravity configurations or floatation systems may be used.

According to one embodiment one or more ballast(s) 38 may be included in the device 40 for allowing one portion of the device 40 such as section 50, which may include lens holder 32 and imager 36, to be usually oriented in a fixed direction, for example, in a counter gravity direction. In alternate embodiments the internal components of a device may be packaged so as to shift the center of gravit and create ballast in one portion of the device, for example, batteries and electronic components may be packaged at one end of an encapsulated system so as to create ballast at that end. Furthermore, additional equipment may not be needed to, for example, alter the buoyancy or specific gravity of the device or to alter the weight distribution of the device, as such configurations may be done with components already part of the device, such as a gas such as air, $CO_2$, $N_2$, etc occurring within the device, etc According to some embodiments of the present invention the device 40 center of gravity may enable the elongated typically empty-spaced dome, such as dome 30 and an optical system, such as lens holder 32 compatible with the refractive index of the air, to float high above the fluid surface so that it is positioned above surface foam and bubbles which can interfere with image quality and field of view. According to some embodiments, when the capsule reaches, for example, the stomach lumen one side of device 40 bearing the optical system compatible for under water imaging will be submerged while the other side of device 40, bearing the imaging system compatible with air imaging will be held high above any interfering surface bubbles or foam, enabling clear imaging of the stomach space Other suitable specific gravities or floating capabilities may allow for other positions of a device within a liquid volume, and other weight or mass configurations may allow for other imaging directions or orientations within a body lumen.

Figure 4A:
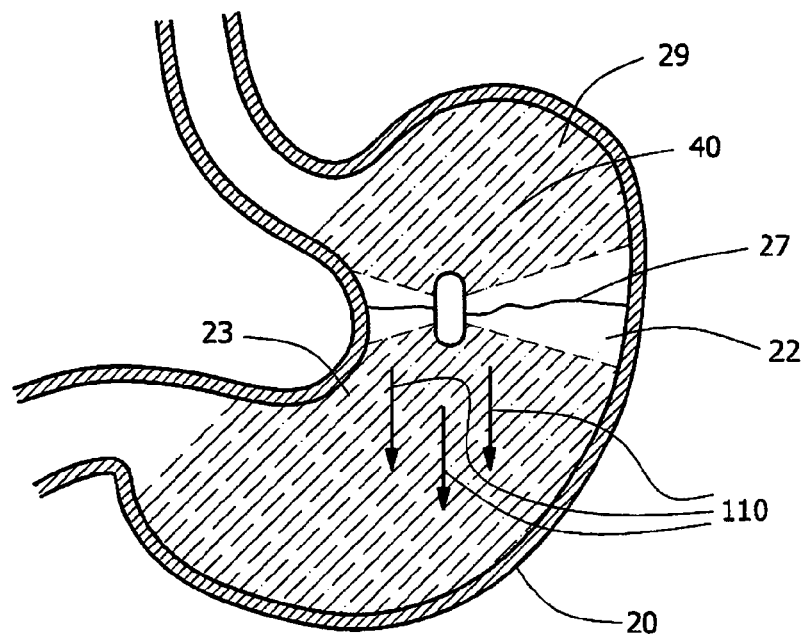
FIGS. 4A and 4B are schematic illustrations of an imaging devices being moved through a body lumen in accordance with an embodiment of the invention.
Figure 4B:
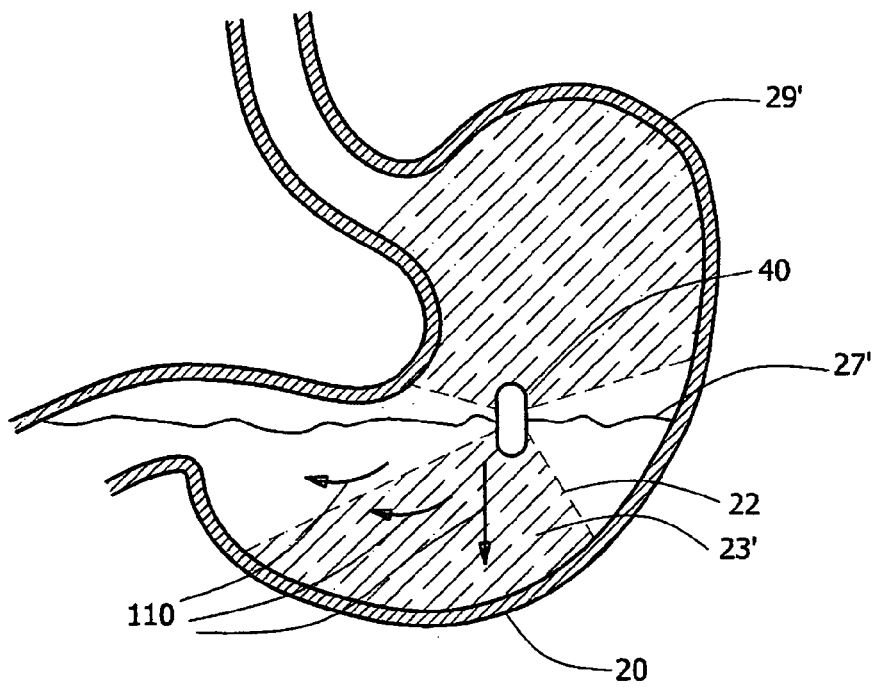

Reference is now made to FIGS. 4A and 4B, which schematically illustrate a sensing device, for example the floatable in-vivo imaging device 40, being moved through a body lumen in accordance with an embodiment of the invention According to one embodiment the floatable in-vivo imaging device 40 may be inserted into a patient's stomach 20, for example, by swallowing. The stomach 20 is filled with a volume of liquid 22, which may be, for example, water, tea, juice, hyperosmolar liquid or any other suitable liquid, which is typically ingested by the patient at about the time of arrival of the device 40 to the stomach 20. According to some embodiments of the present invention, the floatable imaging device 40 will be kept afloat in the liquid 22, enabling the device a multi-directional viewing ability. According to one embodiment the device 40 may include more than one imaging system to enable multi directional viewing and/or imaging. According to some embodiments two imagers, for example imagers 36 and 36' situated on opposing sides or ends of the device 40, may enable multi-directional viewing and/or imaging, for example imaging above and below the liquid level 27. According to one embodiment of the present invention, multi-directional viewing ability may include illumination field and/or a field of view of the area above the liquid level 27, for example area 29. According to other embodiments of the present invention, multi-directional viewing ability may include field of view in the opposite direction, e g. illumination field and/or a field of view of the area below the liquid level 27, for example area 23, that may be for example filled with a volume of liquid 22 The device may be floatable in the sense that its specific gravity is approximately the same or less than a liquid inserted into or known to be in a body lumen. Natural action of the GI tract, including the stomach, typically causes liquids to be emptied from lumens, such as the stomach, within a certain time frame. For example, liquid 22 may be naturally emptied from the stomach 20 over a period of 20-30 minutes, while moving in the direction shown, for example, by arrows 110. The floatable imaging device 40, which is carried by the liquid 22, will thus be moved through the stomach in the general direction of the movement of liquid 22. FIG. 4A, for example, schematically illustrates the stomach 20 at a certain time after ingestion of liquid 22, for example, 1-10 minutes after ingestion of liquid 22, whereas FIG. 4B schematically illustrates the stomach 20 a certain time after that depicted in FIG. 4A, which may be, for example, 1-50 minutes after ingestion of liquid 22. The liquid level 27' in FIG. 4B is shown to be lower than the liquid level 27 in FIG. 4A. Thus, device 40 may obtain images of field of view 29 and/or field of view 23 at a certain time (as seen, for example, in FIG. 2A), whereas, in a certain time following that, device 40 may obtain images of field of view 29' and/or field of view 23' (as shown, for example, in FIG. 4B). Other fields of view may be obtained. For example device 40 may include more than one imaging system, for example, enabling counter-directional viewing.

Figure 5:
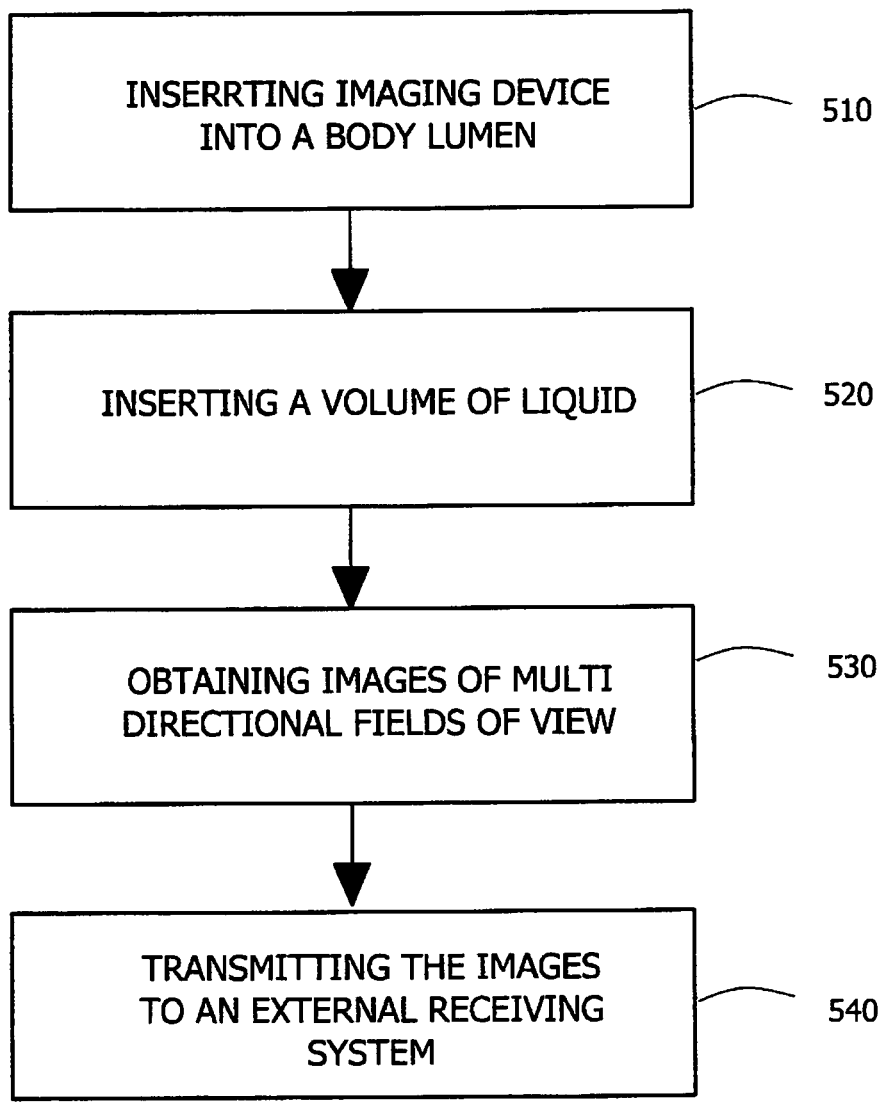
FIG. 5 is a box diagram depicting a method for in-vivo imaging according to an embodiment of the invention.

Reference is now made to FIG. 5, which schematically illustrates a method according to one embodiment of the invention. According to an embodiment of the invention, in block 310, a floatable imaging device is inserted into a patient's body lumen, for example into the large intestine or stomach, e.g., by swallowing the imaging device. In block 320 the patient ingests a volume of liquid, e.g., approximately 100-500 ml of a hyperosmolar liquid, water, tea, juice etc. According to other embodiments the step of inserting the imaging device may be carried out by placing the device in a specific location of the GI tract, for example, by using an endoscope or another suitable inserting device. According to some embodiments ingesting a volume of liquid may precede the step of inserting an imaging device or a volume of liquid can be ingested after the step of inserting an imaging device. According to some embodiments the procedure may be repeated more than once. According to some embodiments the step of ingesting a volume of liquid may be repeated more than once during a procedure whereas each repeat of this step (according to some embodiments after a suitable waiting period, e.g., a minute to tens of minutes between each repeated step) may include ingesting the same or different volumes of liquid and/or different or the same liquids may be used each time. According to some embodiments repeating steps may be utilized for repeated visual scanning or gradual ingestion of a total volume. The total volume may, according to some embodiments, be from approximately 100 ml to a liter or more of liquid. Time periods, absorption periods, amounts, etc., other than specifically disclosed herein may be used. Other operations or series of operations may be used. According to other embodiments a volume of liquid may be inserted into the patient's stomach by means other than by ingesting, for example by injecting the liquid. In block 330 images of multi-directional fields of view may be obtained, for example the field of view may be above the liquid or/and below the liquid. In step 340 the images may be transmitted to an external receiving system, for example to the receiver 90.

According to some embodiments, the device 40 may be made floatable or have its specific gravity changed after insertion into a patient's body. For example, an imaging device 40 may include a buoy or other floatation or weigh element that may be packaged such that it is not buoyant while in packaging. Release of the buoy from its packaging may lend buoyancy to the sensor system. According to some embodiments of the present invention, the buoy may be released from its packaging at a desired location or point in time, such that the floatable in-vivo imaging device may acquire buoyancy according to specific requirements. For example, the floatable in-vivo imaging device 40 according to an embodiment of the invention may be ingested and moved by peristalsis through the esophagus while its buoy is packaged When the device enters the stomach the buoy is released from its packaging (for example, by. using a pH sensitive mechanism, as known in the art, or other suitable mechanism) and the device can then float in a bulk of liquid in the stomach and be carried by the bulk of liquid to all areas of the stomach and may be carried down through the whole stomach, enabling, for example, imaging of substantially most of the stomach walls. The mechanisms by which the buoy is released from its packaging can be externally controlled or automatically controlled, for example, as described in embodiments described in the above mentioned U.S. application Ser. No. 10/150,492.

Figure 6:
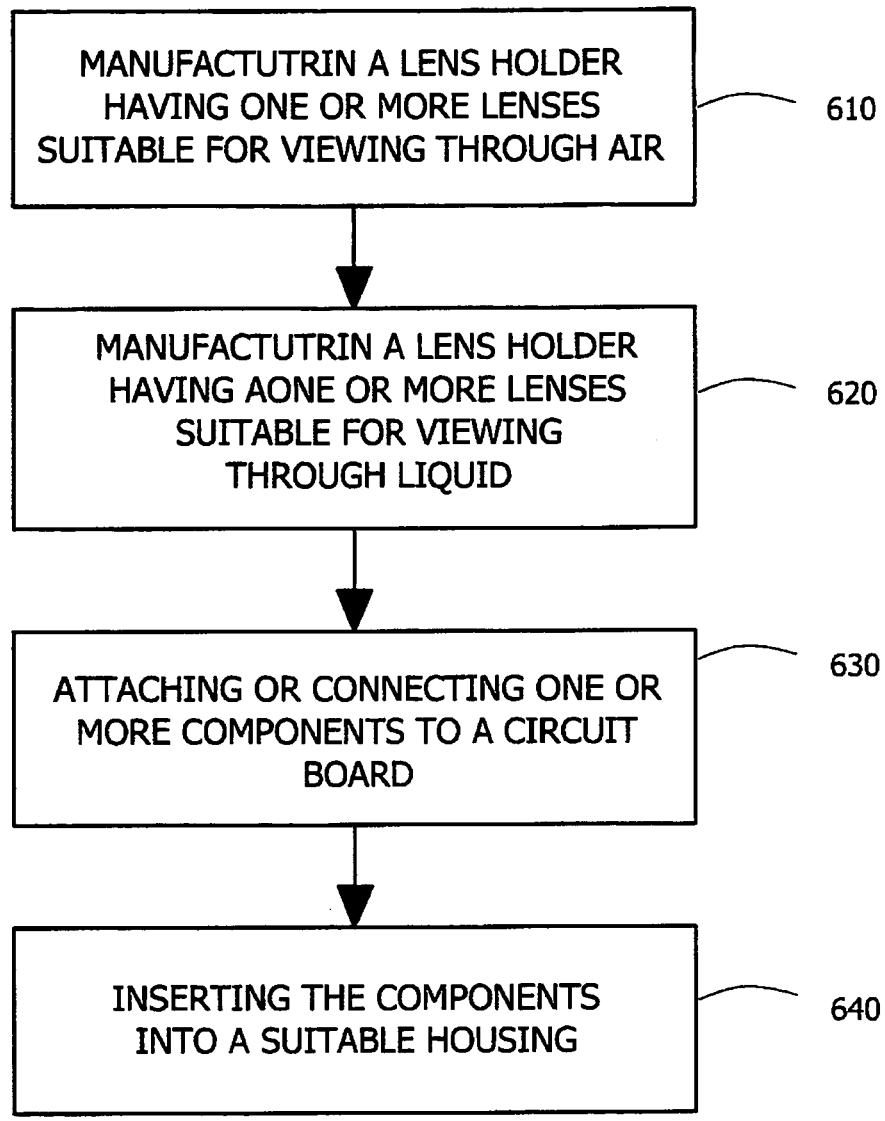
FIG. 6 is a schematic flow-chart of a method of manufacturing a floatable in-vivo imaging device in accordance with some embodiments of the invention.

FIG. 6 is a schematic flow-chart of a method of manufacturing a floatable in-vivo imaging device in accordance with some embodiments of the invention. As indicated at box 610, the method may include manufacturing or providing a lens holder having one or more lenses, suitable for viewing through air. As indicated at box 620, the method may include manufacturing or providing a lens holder having one or more lenses; suitable for viewing through liquid. As indicated at box 630, the method may optionally include attaching or connecting one or more components to a support, for example a circuit board such as a rigid circuit board or a flexible circuit board or a rigid-flex circuit board. This may include, for example, attaching the lens holders, an illumination source, an imager, a power source, a sensor, a transmitter, an antenna, or other suitable components As indicated at box 640, optionally, the method may include inserting the components into a suitable housing adapted or configured for floating in endo luminal fluids and configured for in vivo imaging, for example, a housing of a swallowable capsule.

It will be appreciated by persons skilled in the art that the present invention is not limited by what has been particularly shown and described herein above. Rather the scope of the invention is defined by the claims, which follow.

What is claimed is:

1. A floatable device for in-vivo imaging, said device comprising:
   a first optical system placed behind a first optical dome of said device;
   a second optical system placed behind a second optical dome of said device;
   said first and second optical domes are located at a first and second opposite ends of said device;

said device having a specific gravity of about 1;
wherein the center of gravity of said device is located closer to said first end than to said second end;
wherein said first optical system is compatible with the refractive index of body lumen liquid; and
wherein said second optical system is compatible with the refractive index of a non liquid medium; and
wherein when said device is placed in said body lumen liquid, said center of gravity is to cause said first end to be submerged, while said second end is afloat.

2. The device according to claim 1, wherein each of said optical domes is a transparent empty-spaced elongated optical dome.

3. The device according to claim 1, comprising a lens holder for viewing through said liquid.

4. The device according to claim 1, comprising a planoconcave lens a planoconvex lens and a convex lens.

5. The device according to claim 4, comprising an aperture stop.

6. The device according to claim 5, wherein the aperture stop is placed between said planoconcave lens and said planoconvex lens.

7. The device according to claim 1, comprising a lens holder for viewing through said non liquid medium.

8. The device according to claim 1, further comprising:
a first volume of space having at least an imager and said first and said second optical systems; and
a second volume of space being empty of components, the second volume of space being greater than twice the first volume of space.

9. The device according to claim 1, comprising a control voltage liquid crystal lens.

10. The device according to claim 1, wherein said device is an autonomous swallowable capsule.

11. The device according to claim 1, having a specific gravity of about 1.

12. The device according to claim 1, having a volume to weight ratio that enables said device to float in a body lumen liquid.

13. The device according to claim 1, comprising an illumination source.

14. The device according to claim 1, comprising a transmitter.

15. The device according to claim 1, comprising a ballast.

16. The device according to claim 1, wherein internal components of said device set ballast of the device in one portion of the device.

17. An in-vivo imaging system, said system comprising:
a floatable imaging device having a specific gravity of about 1, said device comprising a
first optical system placed behind a first optical dome of said device,
a second optical system placed behind a second optical dome of said device;
said first and second optical domes are respectively located at a first and a second opposite ends of said device;
a transmitter; and
a receiver,
wherein the center of gravity of said device is located closer to said first end than to said second end;
wherein said first optical system is compatible with the refractive index of a body lumen liquid; and
wherein said second optical system is compatible with the refractive index of a non liquid medium; and
wherein when said device is placed in said body lumen liquid, said center of gravity is to cause said first end to be submerged, while said second end is afloat.

18. The system according to claim 17, comprising a data processor.

19. The system according to claim 17, comprising a storage unit.

20. The system according to claim 17, comprising a monitor.

* * * * *